United States Patent
Huang et al.

(10) Patent No.: US 7,108,834 B2
(45) Date of Patent: Sep. 19, 2006

(54) DEVICE FOR PRODUCING NEGATIVE ION FRAGRANCE

(76) Inventors: Chuan Pan Huang, P.O. Box 2-10, Tainan City (TW); Chen Lung Huang, P.O. Box 2-10, Tainan City (TW)

( * ) Notice: Subject to any disclaimer, the term of this patent is extended or adjusted under 35 U.S.C. 154(b) by 223 days.

(21) Appl. No.: 10/966,898

(22) Filed: Oct. 14, 2004

(65) Prior Publication Data

US 2006/0083665 A1 Apr. 20, 2006

(51) Int. Cl.
  *A62B 7/08* (2006.01)
  *A61L 9/03* (2006.01)
  *A61L 9/22* (2006.01)
(52) U.S. Cl. ............... 422/123; 422/120; 422/306; 239/34; 239/44
(58) Field of Classification Search ............... 422/120, 422/123, 306; 239/34, 44
See application file for complete search history.

(56) References Cited

U.S. PATENT DOCUMENTS 5,196,171 A * 3/1993 Peltier .................. 422/121
6,713,024 B1 * 3/2004 Arnell et al. ............... 422/124
6,877,271 B1 * 4/2005 Hughes et al. .............. 43/124

FOREIGN PATENT DOCUMENTS

| JP | 2004166731 A | * | 6/2004 |
|----|---|---|---|
| TW | 00547087 | | 8/1991 |
| TW | 00568747 | | 8/1991 |
| TW | 00564751 | | 2/1992 |
| TW | M240223 | | 11/1992 |

* cited by examiner

*Primary Examiner*—Krisanne Jastrzab
*Assistant Examiner*—Sean E. Conley

(57) ABSTRACT

A device for producing negative ion fragrance includes a basic body and a negative ion producer. The basic body is formed with a volatilizing cavity in the center for receiving therein the neck of a fragrant essential oil bottle or a fragrant essential oil bottle. The negative ion producer is provided with a negative ion shooting unit extending in the volatilizing cavity of the basic body. Negative ion produced by the negative ion shooting unit is mixed with the fragrant essential oil in the volatizing cavity and then their mixed vapor is sent out for use, elevating effect in use of fragrant essential oil.

3 Claims, 4 Drawing Sheets

DEVICE FOR PRODUCING NEGATIVE ION FRAGRANCE

FIELD OF THE INVENTION

This invention relates to a device for producing negative ion fragrance, particularly to one composed of a basic body and a negative ion producer. The basic body is formed with a volatilizing cavity in the center for the negative ion shooting unit of the negative ion producer to be installed therein. The negative ion produced by the negative ion shooting unit is mixed and vaporized with the fragrant essential oil in the volatilizing cavity of the basic body and then their mixed vapor is sent out for use, elevating useful effect of fragrant essential oil.

BACKGROUND OF THE INVENTION

A first kind of conventional fragrant oil volatilizing device is a multi-functional wall electric vaporizer, as disclosed in a Taiwan patent No. 568747 (European Patent Alliance 81, No. 01830528.4, Applicants: S.C.JOHNSON & SON, INC.). Such a wall electric vaporizer is provided with a container for receiving therein a bottle with liquid and a wick, and an electric heater for heating the wick of the bottle to volatilize the liquid in the bottle.

A second kind of conventional fragrant oil volatilizing device is a bactericide and fragrant oil volatilizing device installed inside an automobile, as disclosed in a Taiwan patent No. 240223. Such a device is provided with a power socket to be fixed inside an automobile and a negative ion producer on an electronic base board for carrying out sterilization. The electronic base board is provided with a heater received in a secondary chamber for heating and evaporating the fragrant oil in the secondary chamber.

A third kind of conventional fragrant oil volatilizing device is a whirlwind-typed vapor negative ion fragrance producing device, as disclosed in a Taiwan patent No. 564751. This device is provided with a rotary disk driven to rotate by a motor and having a plurality of arc-shaped blades spaced apart to make up an air current producer that can be driven to produce high-speed air current for stirring up the liquid in a container to produce negative ion.

A fourth kind of conventional fragrant oil volatilizing device is a drug or fragrant oil or essential oil vaporizer, as disclosed in a Taiwan patent No. 547087. This vaporizer is provided with a supersonic oscillator at the bottom of a container for evaporating the drug or the fragrant oil or the essential oil in the container.

The above-mentioned four kinds of conventional fragrant oil volatilizing devices carry out volatilization of fragrant oil either by electric heating or by high-speed rotation of the blades of the air current producer or by vibration of the supersonic oscillator, but none of these devices makes use of negative ion to directly volatilize essential oil; nor is the marked effect of the negative ion mentioned in these devices.

SUMMARY OF THE INVENTION

The objective of the invention is to offer a device for producing negative ion fragrance, provided with a negative ion producer having a negative ion shooting unit extending in the volatilizing cavity of a basic body. The negative ion produced by the negative ion shooting unit is mixed and vaporized with the fragrant essential oil in the volatilizing cavity and then their mixed vapor is sent out for use, greatly elevating useful effect of fragrant essential oil.

The features of the invention are described as follows.

1. The device for producing negative ion fragrance has a basic body formed with a volatilizing cavity in the center for receiving therein the neck of a fragrant essential oil bottle or a fragrant essential oil bottle.

2. The device for producing negative ion fragrance is provided with a negative ion producer having a negative ion shooting unit extending in the volatilizing cavity of the basic body. The negative ion produced by the negative ion shooting unit is mixed and vaporized with the fragrant essential oil in the volatilizing cavity and then their mixed vapor is sent out for use.

BRIEF DESCRIPTION OF DRAWINGS

This invention will be better understood by referring to the accompanying drawings, wherein.

DETAILED DESCRIPTION OF THE PREFERRED EMBODIMENT

Figure 1:
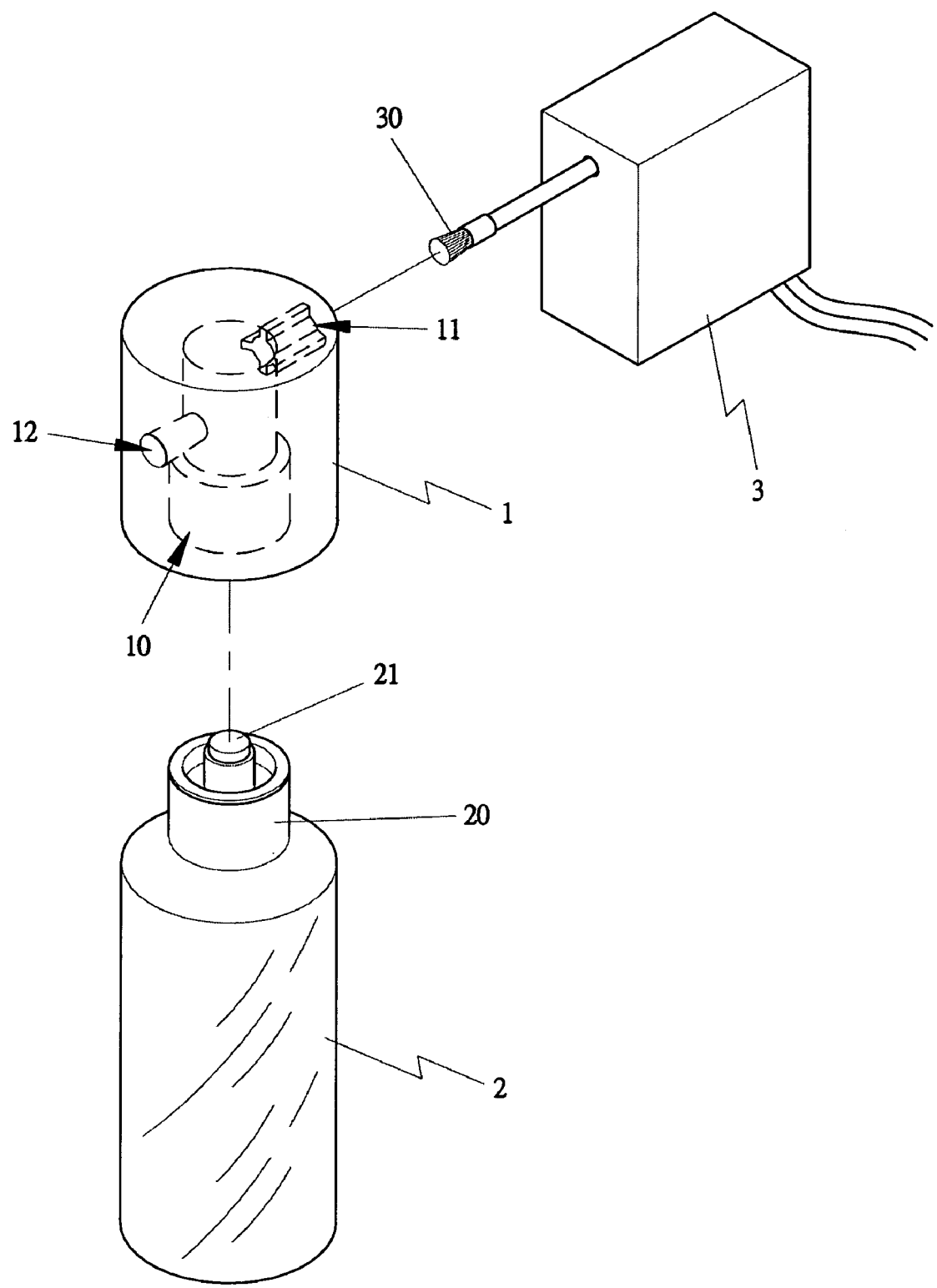
FIG. 1 is an exploded perspective view of a first preferred embodiment of a device for producing negative ion fragrance in the present invention.
Figure 2:
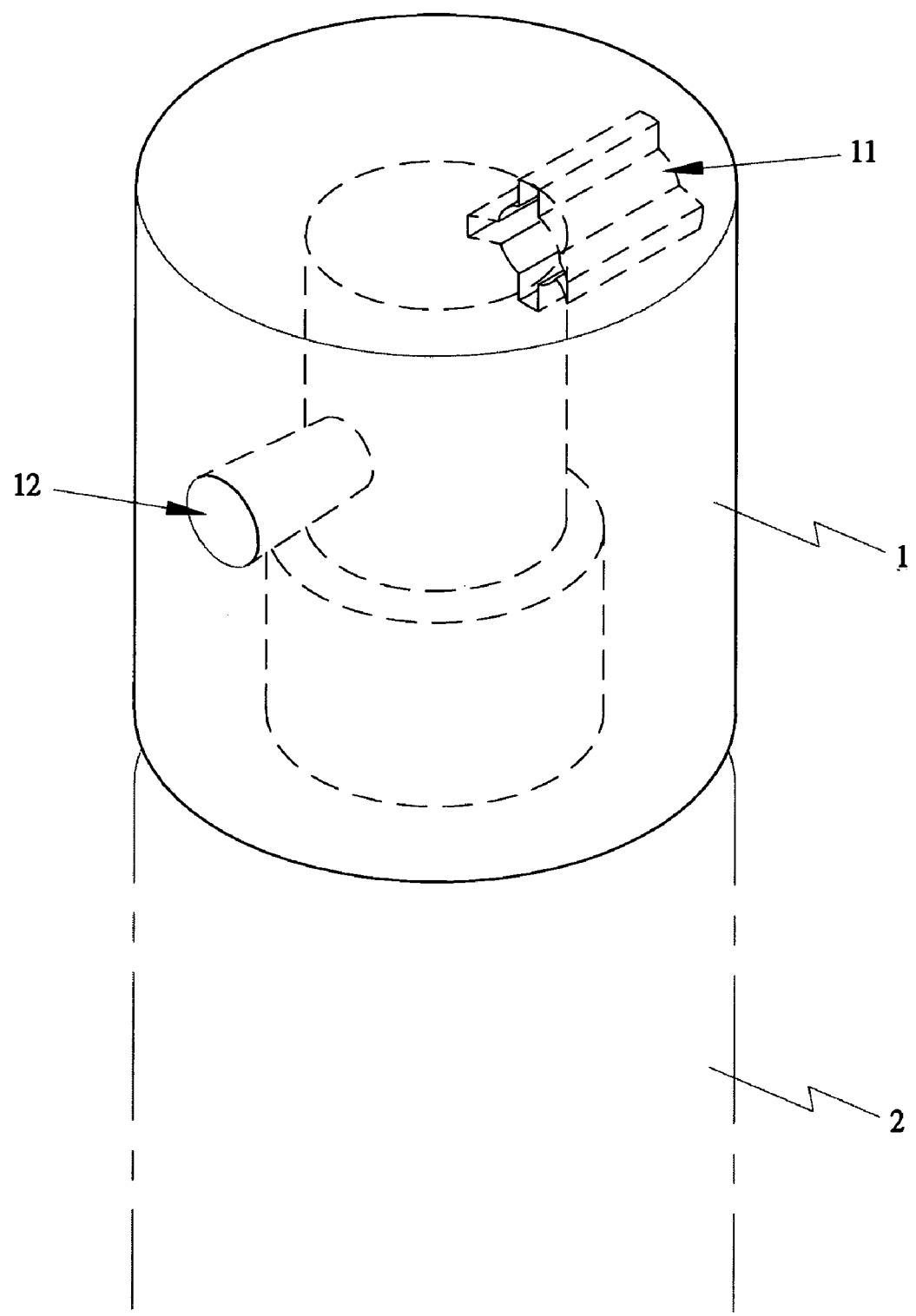
FIG. 2 is a perspective view of the first preferred embodiment of a device for producing negative ion fragrance in the present invention.

A first preferred embodiment of a device for producing negative ion fragrance in the present invention, as shown in FIGS. 1 and 2, includes a basic body 1, a negative ion producer 3 combined together.

The basic body 1 is formed with a volatilizing cavity 10 in the center for receiving therein the neck 20 of a fragrant essential oil bottle 2, as shown in FIG. 2, letting the wick 21 of the fragrant essential oil bottle 2 positioned in the volatilizing cavity 10. The wick 21 is able to volatilize the fragrant essential oil in the fragrant essential oil bottle 2 in the volatilizing cavity 10. Further, the basic body 1 is bored with two slots 11 and 12 through its wall, and the slot 11 is for fitting therein the negative ion shooting unit 30 of the negative ion producer 3 while the slot 12 for sending out the mixed vapor of the negative ion with the fragrant essential oil in the volatilizing cavity 10.

The negative ion producer 3 is provided with the negative ion shooting unit 30 fitted in the slot 11 and extending in the volatilizing cavity 10 of the basic body 1. Thus, negative ion produced by the negative ion shooting unit 30 can be mixed and vaporized with the fragrant essential oil in the volatilizing cavity 10 and then their mixed vapor is sent out for use.

Figure 3:
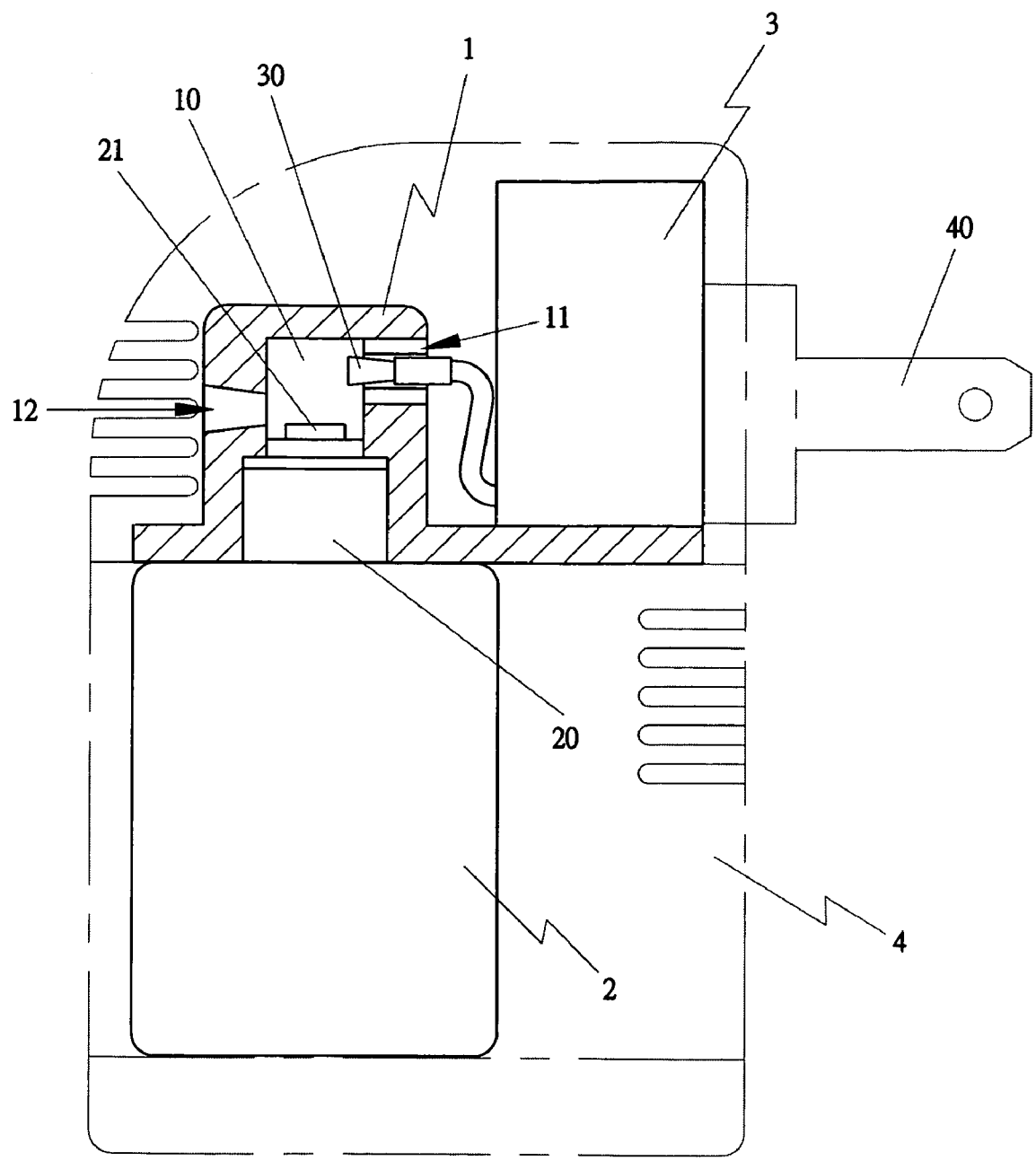
FIG. 3 is a side cross-sectional view of a second preferred embodiment of a device for producing negative ion fragrance in the present invention.

A second preferred embodiment of a device for producing negative ion fragrance in the present invention, as shown in FIG. 3, includes a basic body 1, a negative ion producer 3 and a casing 4 combined together.

The basic body 1 is formed with a volatilizing cavity 10 in the center for receiving therein the neck 20 of a fragrant essential oil bottle 2, letting the wick 21 of the fragrant essential oil bottle 2 positioned in the volatilizing cavity 10 for volatilizing the fragrant essential oil in the volatilizing cavity 10. Further, the basic body 1 is bored with two slots 11 and 12 through its wall, and the slot 11 is for fitting therein the negative ion shooting unit 30 of the negative ion producer 3 while the slot 12 for sending out the mixed vapor of the negative ion with the fragrant essential oil in the volatilizing cavity 10.

The negative ion producer 3 is provided with the negative ion shooting unit 30 fitted in the slot 11 and extending in the volatilizing cavity 10 of the basic body 1. Thus, negative ion produced by the negative ion shooting unit 30 can be mixed and vaporized with the fragrant essential oil in the volatilizing cavity 10 and then their mixed vapor is sent out for use.

The casing 4 is provided for receiving therein the basic body 1, the fragrant essential oil bottle 2 and the negative ion producer 3. The casing 4 is provided with a plug 40 to plug in an indoor socket so that the device can produce fragrant essential oil containing negative ion, elevating effect in use of the fragrant essential oil.

Figure 4:
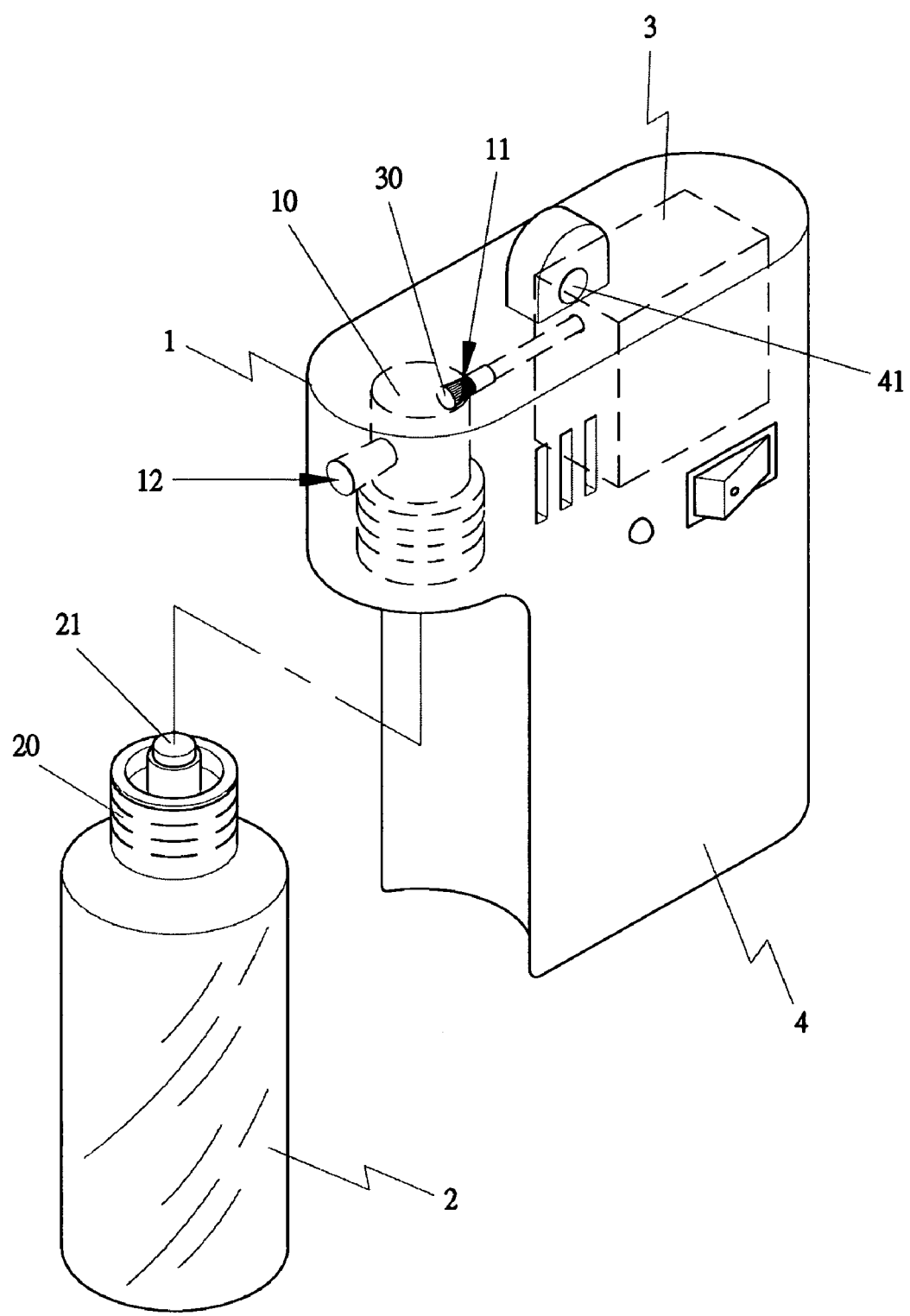
FIG. 4 is a partial exploded perspective view of a third preferred embodiment of a device for producing negative ion fragrance in the present invention.

A third preferred embodiment of a device for producing negative ion fragrance in the present invention, as shown in FIG. 4, includes a basic body 1, a negative ion producer 3 and a casing 4 combined together.

The basic body 1 is formed with a volatilizing cavity 10 in the center for receiving therein the neck 20 of a fragrant essential oil bottle 2, letting the wick 21 of the fragrant essential oil bottle 2 positioned in the volatilizing cavity 10 for volatilizing the fragrant essential oil in the fragrant essential oil bottle 2. The basic body 1 is further bored with two slot 11, 12 through its wall, and the slot 11 is for receiving the negative ion shooting unit 30 of the negative ion producer 3 while the slot 12 for sending out the mixed vapor of the negative ion with the fragrant essential oil.

The negative ion producer 3 is provided with the negative ion shooting unit 30 fitted in the slot 11 and extending in the volatilizing cavity 10 of the basic body 1. Thus, negative ion produced by negative ion shooting unit 30 can be mixed and vaporized with the fragrant essential oil in the volatilizing cavity 10 and then their mixed vapor is sent out for use.

The casing 4 is provided for receiving the basic body 1, the essential oil bottle 2 and the negative ion producer 3. The casing 4 is provided with a plug 40 to plug in an indoor socket and bored with hang hole 41 for hanging the casing 4 on a wall.

While the preferred embodiments of the invention have been described above, it will be recognized and understood that various modifications may be made therein and the appended claims are intended to cover all such modifications that may fall within the spirit and scope of the invention.

What is claimed is:

1. A device for producing negative ion fragrance comprising:
    a basic body formed with a volatilizing cavity in the center, said volatilizing cavity receiving therein the neck of a fragrant essential oil bottle, the fragrant essential oil in said fragrant essential oil bottle volatilizing in said volatilizing cavity, said basic body bored with two slots through its wall, one of said two slots provided for fitting a negative ion shooting unit of a negative ion producer, the other one of said two slots provided for sending out mixed vapor of negative ion with fragrant essential oil: and
    said negative ion producer provided with said negative ion shooting unit, said negative ion shooting unit received in one of said two slots and extending in said volatilizing cavity of said basic body.

2. The device for producing negative ion fragrance as claimed in claim 1, wherein the wick of said fragrant essential oil bottle is positioned in said volatilizing cavity of said basic body so that fragrant essential oil in said fragrant essential oil bottle can be volatilized in said volatilizing cavity through said wick.

3. A device for producing negative ion fragrance comprising:
    a basic body formed with a volatilizing cavity in the center, said volatilizing cavity receiving therein a fragrant essential oil bottle, fragrant essential oil in said fragrant essential oil bottle volatilized in said volatilizing cavity, said basic body bored with two slots through its wall, one of said two slots provided for fitting a negative ion shooting unit of said negative ion producer, the other one of said two slots for sending out mixed vapor of negative ion with fragrant essential oil:
    said negative ion producer provided with said negative ion shooting unit, said negative ion shooting unit fitted in one of said two slots and extending in said volatilizing cavity of said basic body: and
    a casing provided for receiving therein said basic body and said essential oil bottle and said negative ion producer, said casing provided with a plug.

* * * * *